United States Patent
Kluft

(10) Patent No.: US 11,933,794 B2
(45) Date of Patent: Mar. 19, 2024

(54) METHOD FOR DETERMINING FACTOR XA INHIBITOR DOSAGE

(71) Applicant: Good Biomarker Sciences B.V., Sassenheim (NL)

(72) Inventor: Cornelis Kluft, Sassenheim (NL)

(73) Assignee: Good Biomarker Sciences B.V., Sassenheim (NL)

( * ) Notice: Subject to any disclaimer, the term of this patent is extended or adjusted under 35 U.S.C. 154(b) by 795 days.

(21) Appl. No.: 16/761,769

(22) PCT Filed: Nov. 1, 2018

(86) PCT No.: PCT/NL2018/050730
§ 371 (c)(1),
(2) Date: May 5, 2020

(87) PCT Pub. No.: WO2019/088838
PCT Pub. Date: May 9, 2019

(65) Prior Publication Data
US 2021/0181213 A1    Jun. 17, 2021

(30) Foreign Application Priority Data

Nov. 6, 2017  (NL) ..................................... 2019854

(51) Int. Cl.
*G01N 33/86*  (2006.01)

(52) U.S. Cl.
CPC ....... *G01N 33/86* (2013.01); *G01N 2333/755* (2013.01)

(58) Field of Classification Search
None
See application file for complete search history.

(56) References Cited

U.S. PATENT DOCUMENTS 6,211,341 B1 * 4/2001 Zeelon .................. A61K 38/58
                                                      530/382

FOREIGN PATENT DOCUMENTS

| WO | WO-9309804 A1 * | 5/1993 | ........... C07K 14/755 |
| WO | WO-0007626 A1 * | 2/2000 | ................ A61P 7/02 |
| WO | 2017/197332 A1 | 11/2017 | |

OTHER PUBLICATIONS

Bonar et al., Pathology. Jan. 2016;48(1):60-71. doi: 10.1016/j.pathol. 2015.11.025. Epub Dec. 17, 2015. PMID: 27020211.*
Chandler et al., Am J Clin Pathol. Jul. 2003;120(1):34-9. doi: 10.1309/C8T8-YNB4-G3W4-5PRF.*
Waxman et al., Science. May 4, 1990;248(4955):593-6. doi: 10.1126/science.2333510.*
Glauser et al. Thromb Haemost. Dec. 2009; 102(6):1183-1193. doi: 10.1160/TH09-04-0273.*
Melo et al., J Biol Chem. May 14, 2004;279(20):20824-35. doi: 10.1074/jbc.M308688200. Epub Mar. 2, 2004. PMID: 14996843.*
Prescribing Information for ELIQUIS® (apixaban) tablets, initial U.S. approval 2012, 15 pages, downloaded from / packageinserts. bms.com/pi/pi_eliquis.pdf.*
Prescribing Information for SAVAYSA (edoxaban) tablets, Initial U.S. Approval: 2015, 34 pages, downloaded from / daiichisankyo. us/prescribing-information-portlet/getPIContent?productName=Savaysa&inline=true.*
Prescribing Information for XARELTO (rivaroxaban) Initial U.S. Approval: 2011, 34 pages, downloaded from / www.janssenlabels. com/package-insert/product-monograph/prescribing-information/XARELTO-pi.pdf.*
Adcock et al., "Direct Oral Anticoagulants (DOACs) in the Laboratory: 2015 Review", Thrombosis research, vol. 136, No. 1, (May 8, 2015, pp. 7-12.
Bonar et al., "The effect of the direct factor Xa inhibitors apixaban and rivaroxaban on haemostasis tests: a comprehensive assessment using in vitro and ex vivo samples", Pathology., vol. 48, No. 1, (Jan. 1, 2016), pp. 60-71.
International Search Report for International Application No. PCT/NL2018/050730, dated Feb. 27, 2019, 6 pages.
International Written Opinion for International Application No. PCT/NL2018/050730, dated Feb. 27, 2019, 9 pages.
Katarzyna et al., "The use of direct oral anticoagulants in 56 patients with antiphospholipid syndrome", Thrombosis Research, vol. 152, (Dec. 14, 2016), pp. 93-97.
Martin et al., "How I treat patients with inherited bleeding disorders who need anticoagulant therapy", Blood, vol. 128, No. 2, Apr. 22, 2016, pp. 178-184.
Eaton et al "Proteolytic processing of human factor VIII. Correlation of specific cleavages by thrombin, factor Xa, and activated protein C with activation and inactivation of factor VIII coagulant activity" Biochemistry. Jan. 2, 19868,25(2):505-12 (Abstract Only).
Jespersen et al. "Laboratory Techniques in Thrombosis—a Manual" Springer Science+Business Media Dordrecht 1999).
Kitchen et al. on behalf of the WFH Laboratory Sciences Committee. "Diagnosis of Hemophilia and Other Bleeding Disorders" A Laboratory Manual, 2nd Edition. Montreal, Quebec, Canada: World Federation of Hemophilia, 2010).

(Continued)

*Primary Examiner* — Michael Szperka
(74) *Attorney, Agent, or Firm* — TraskBritt

(57) ABSTRACT

A method of detecting Factor VIII level in a subject, particularly in a subject in need of treatment with at least one Factor Xa inhibitor. The method comprises (a) selecting at least one subject in need of treatment with at least one Factor Xa inhibitor; and (b) detecting Factor VIII level in a sample obtained from the at least one subject with the aim to determine an appropriate dosage of the at least one Factor Xa inhibitor. Preferably, the method comprises a further step of administering at least one Factor Xa inhibitor to the subject.

6 Claims, 4 Drawing Sheets

(56) References Cited

OTHER PUBLICATIONS

Langdell et al. "Effect of antihemophilic factor on one-stage clotting tests; a presumptive test for hemophilia and a simple one-stage antihemophilic factor assy procedure" Translational Research, 1953, vol. 41, Issue 4, pp. 637-647.
Malm et al "Blood plasma reference material: a global resource for proteomic research" J Proteome Res. Jul. 5, 2013;12(7):3087-92 (Abstract Only).
O'Donnell et al "High prevalence of elevated factor VIII levels in patients referred for thrombophilia screening: role of increased synthesis and relationship to the acute phase reaction" Thromb Haemost. May 1997; 77:825-828.
Rosén et al. "Chromogenic determination of factor VIII activity in plasma and factor" VIII concentrates. Chromogenic Monograph Series (2006).
Soshitova et al "Predicting prothrombotic tendencies in sepsis using spatial clot growth dynamics " Blood Coagul Fibrinolysis. Sep. 2012;23(6):498-507 (Abstract Only).
European Communication pursuant to Article 94(3) EPC for European U.S. Appl. No. 18/812,385, dated Mar. 3, 2023, 5 pages.

\* cited by examiner

METHOD FOR DETERMINING FACTOR XA INHIBITOR DOSAGE

CROSS-REFERENCE TO RELATED APPLICATIONS

This application is a national phase entry under 35 U.S.C. § 371 of International Patent Application PCT/NL2018/050730, filed Nov. 1, 2018, designating the United States of America and published in English as International Patent Publication WO 2019/088838 A1 on May 9, 2019, which claims the benefit under Article 8 of the Patent Cooperation Treaty to The Netherlands Patent Application Serial No. 2019854, filed Nov. 6, 2017.

TECHNICAL FIELD

The disclosure relates to a method for determining an appropriate dosage of a Factor Xa inhibitor for a subject in need of treatment with the Factor Xa inhibitor.

BACKGROUND

Anticoagulant therapy aims for the prevention and treatment of thromboembolic diseases. The currently available therapeutic anticoagulants include low-molecular-weight heparins and vitamin K antagonists. In addition, a new class of direct oral anticoagulants (DOAC) has been developed in the last decade that overcome some of the main drawbacks of traditional anticoagulants, such as the need for parenteral administration, the onset of thrombocytopenia in the case of heparins, and the need for routine International Normalized Ratio (INR) monitoring and the known susceptibility to a number of food/drug interactions for the Vitamin K antagonists.

Two types of DOACs are currently available: the Factor Xa inhibitors, such as apixaban, edoxaban, and rivaroxaban, and the thrombin inhibitors, such as dabigatran. Unlike Vitamin K antagonists, which block the formation of multiple, active vitamin K-dependent coagulation factors, DOACs antagonize the activity of a single step in coagulation. Most comparisons between vitamin K antagonists and DOACs are based on their ability to reduce the incidence of life-threatening bleeding complications where the dosage turns out to be too high.

Currently, clinical trials suggest that bleeding rates with DOAC are generally the same or lower than the bleeding rates with Vitamin K antagonists. Owing to their efficacy and safety profile, DOACs are being increasingly used in clinical practice worldwide.

However, real-life efficacy data suggest that DOAC-associated bleeding events remain a problem. The management thereof can be a major concern for physicians because of the current specific antidotes to reverse their anticoagulant effects. Until an antidote becomes widely available, supportive care is required for the treatment of hemorrhagic complications, for example, with the use of fresh-frozen plasma, prothrombin complex concentrates, or recombinant activated Factor VIIa. Furthermore, an assessment of coagulation status is necessary in the case of major bleeding, trauma, urgent surgery or overdose.

Therefore, there remains a need to improve the current treatment with DOACs and, in particular, to optimize the current treatment with Factor Xa inhibitors.

BRIEF SUMMARY

The disclosure provides for a method, e.g., for determining an appropriate dosage of at least one Factor Xa inhibitor for a subject in need of treatment with at least one Factor Xa inhibitor or of detecting Factor VIII level, particularly in a subject in need of treatment with at least one Factor Xa inhibitor, wherein the method comprises:
  (a) selecting at least one subject in need of treatment with at least one Factor Xa inhibitor;
  (b) detecting Factor VIII level in a sample obtained from the at least one subject.

Treatment with the at least one anti-coagulant, preferably (reversible) Factor Xa inhibitor such as apixaban, can be prescribed in the case of thromboembolic diseases, for example, a condition chosen from the group consisting of: thrombosis, venous thrombosis, thromboembolic disease, thrombosis prophylaxis particularly after surgery, cardiovascular disease, coronary artery disease, angina pectoris, angina infarction, myocardial infarction, atrium fibrillation, stroke, ischemic stroke, cerebral infarction, transient ischemic attack, cancer-associated thrombosis, and pulmonary embolism.

It has been found that subjects having different Factor VIII concentrations in their blood plasma benefit from a different dose of anti-coagulant, i.e., Factor Xa inhibitor. In particular, a lower Factor VIII blood plasma concentration warrants a lower dose of anti-coagulant, i.e., Factor Xa inhibitor, and a higher Factor VIII blood plasma concentration warrants a higher dose of anti-coagulant, i.e., Factor Xa inhibitor.

This disclosure reveals the more precise role of Factor Xa in clot growth experiments comparing normal and hemophilia plasma (the latter being deficient in Factor IX and Factor VIII). In the hemophilia plasmas, the inhibitors rivaroxaban, apixaban and edoxaban did not inhibit clot growth, in contrast to what was found in normal plasma. This demonstrates that Factor Xa, in its role in fibrin formation for clotting (activating prothrombin to thrombin), was not inhibited in the hemophilia plasmas. In view thereof, it was considered that inhibition of Factor Xa in normal plasma could concern the additional factors that are absent in hemophilia plasmas, notably Factor IX and Factor VIII. It has previously been suggested that Factor Xa may initially activate and subsequently inactivate Factor VIII by proteolytic processing (Eaton et al., Biochemistry 1986, 25: 505-12), but the significance of these proteolytic events was not known. For clot growth, this now appears the key mechanism. In contrast, in text books, activation of Factor VIII is indicated to be a thrombin action.

Without being bound by any theory, it has been considered that Factor Xa inhibitors inhibit the Factor VIIIa activation in clot growth. This provides a rationale for the dependence of the inhibition on Factor VIII levels, as Factor VIII competes as substrate for Factor Xa with the Factor Xa inhibitor. Thus, a higher Factor VIII reduces the efficacy of a Factor Xa inhibitor in a competitive manner.

FIG. 1, for example, shows that for a Factor VIII level of below 100%, the lowest anti-coagulant concentration (apixaban) already achieves close to maximal inhibition of clot rate. Here, treatment with a low anti-coagulant concentration can be indicated (to achieve a plasma concentration of ~0.1 µM) to not create a bleeding risk. For factor VIII levels above 100%, 0.1 apixaban may not be very effective and 0.35 µM is suggested for substantial inhibition. Here, the treatment is aimed at reducing thrombosis risk.

In step (b) of the method, the detection of Factor VIII is preferably performed by an ELISA assay, one-stage clotting assay or chromogenic assay, preferably an ELISA assay. These assays are further described in the Example section. The one-stage clotting assay or chromogenic assay can be applied before treatment with Factor Xa inhibitor, and preferably not during the treatment, whereas the ELISA assay can be applied before and/or during treatment with Factor Xa inhibitor.

In the method of the disclosure, step (b) can be used to determine an appropriate dosage of the at least one Factor Xa inhibitor or other anti-coagulant, preferably wherein the dosage (per time period such as per day, week, month, preferably per day) of the at least one Factor Xa inhibitor is
between 0.01 and 20 mg, 0.01 and 18 mg, 0.05 and 16 mg, 0.1 and 14 mg, 0.5 and 12 mg, or 0.75 and 10 mg, preferably between 1 mg and 10 mg in case the Factor VIII level as detected is below at least one reference value; or
between 5 and 50 mg, 6 and 45 mg, 7 and 40 mg, 8 and 35 mg, or 9 and 32 mg, preferably between 10 mg and 30 mg in case the Factor VIII level as detected is above at least one reference value.

The reference value can be a Factor VIII level of between 50% and 200%, 60% and 200%, 50% and 75%, 75% and 100%, 70% and 200%, 80% and 175%, 80% and 160%, or between 80% and 140%, or 150% and 200 or 250%, preferably between 100% and 150% with respect to the Factor VIII level in standard plasma, for example, as measured by a one-stage clotting assay or chromogenic assay, preferably by an ELISA assay, all as described in the Example. Standard plasma can be obtained as described by Malm et al. (J. Proteome Res. 2013 Jul. 5; 12(7):3087-92). Preferably, the standard plasma is WHO International Standard plasma, more preferably, WHO International Standard plasma 07/316 for Blood Coagulation Factor VIII and Von Willebrand Factor in Plasma (6th I.S.) or WHO International Standard plasma 07/350 for Blood Coagulation Factor VIII Concentrate (8th I.S.), as obtainable from, e.g., NIBSC.

Preferably, step (b) is performed after step (a). Furthermore, step (b) may be performed before treatment of the at least one subject with the at least one Factor Xa inhibitor, for example, to determine an appropriate starting dose. Step (a) may be optional and may be applied with respect to subjects whose Factor VIII level is unknown and/or whose Factor VIII level has not previously been measured.

Additionally and/or alternatively, step (b) may be performed during treatment of the at least one subject with the at least one Factor Xa inhibitor, for example, to determine if, due to a change in Factor VIII level, the dose of the Factor Xa inhibitor should be increased or decreased. The treatment may, for example, be periodic administration of the at least one Factor Xa inhibitor. Accordingly, step (b) may be repeated over time, for example, at least one, two, three, five or ten time(s), preferably with interval(s) of between 1-500, 5-250, or 10-100 days.

Factor VIII (FVIII) is a blood-clotting protein, also known as anti-hemophilic factor (AHF). In humans, Factor VIII is encoded by the F8 gene. Defects in this gene result in hemophilia A, a recessive X-linked coagulation disorder. Factor VIII is produced in liver sinusoidal cells and endothelial cells outside of the liver throughout the body. This protein circulates in the bloodstream in an inactive form, bound to another molecule called von Willebrand factor, until an injury that damages blood vessels occurs. In response to injury, coagulation factor VIII is activated and separates from von Willebrand factor. The active protein (sometimes written as coagulation Factor VIIIa) interacts with another coagulation factor called factor IX. This interaction sets off a chain of additional chemical reactions that form a blood clot.

People with high levels of factor VIII are at increased risk for deep vein thrombosis and pulmonary embolism.

Anti-coagulants in the context of the present disclosure may come in different types, for example, low-molecular-weight heparin, vitamin K antagonist, or a direct oral anticoagulant (DOAC). DOACs are particularly preferred in the present disclosure, and include thrombin inhibitors, such as dabigatran, but more preferred is the use of a Factor Xa inhibitor (also referred to as Xabans).

Indirect or direct Factor Xa inhibitors may be used. Fondaparinux is an example of a synthetic indirect inhibitor of Factor Xa. Its chemical structure is based on the natural pentasaccharide contained within heparin and LMWHs. It potentiates the rate of neutralization of Factor Xa by anti-thrombin and does not inactivate thrombin.

Fondaparinux does not inhibit Factor Xa bound in the prothrombinase complex and, therefore, does not completely inhibit Factor Xa. Fondaparinux can be administered via subcutaneous injection, which may limit long-term use.

Direct Factor Xa inhibitors include rivaroxaban (Xarelto) from Bayer, apixaban (Eliquis) from Bristol-Myers Squibb, betrixaban from Portola Pharmaceuticals, darexaban (YM150) from Astellas, edoxaban (Lixiana) from Daiichi, otamixaban by Sanofi, and more recently letaxaban (TAK-442) from Takeda and eribaxaban (PD0348292) from Pfizer.

Particularly preferred are rivaroxaban, edoxaban and specifically apixaban. They directly engage the active site of the Factor Xa molecule. Typically, rivaroxaban, apixaban and edoxaban are administered orally.

Preferably, the method according to the present disclosure is performed in vitro and/or ex vivo. The sample as referred to herein may thus be a body fluid sample, for example, a blood sample or blood plasma sample.

As will be clear to the skilled person, the method according to the present disclosure may further comprise a step (c) of administering the at least one Factor Xa inhibitor to the subject, preferably orally. The Factor Xa inhibitor may be administered, for example, once or twice daily.

The present disclosure also provides for the use of a kit comprising means for detecting Factor VIII, for determining an appropriate dosage of at least one Factor Xa inhibitor for a subject in need of treatment with at least one Factor Xa inhibitor, preferably wherein the dosage per day of the at least one Factor Xa inhibitor is
between 0.01 and 20 mg, 0.01 and 18 mg, 0.05 and 16 mg, 0.1 and 14 mg, 0.5 and 12 mg, or 0.75 and 10 mg, preferably between 1 mg and 10 mg if the Factor VIII level is below at least one reference value; or
between 5 and 50 mg, 6 and 45 mg, 7 and 40 mg, 8 and 35 mg, or 9 and 32 mg, preferably between 10 mg and 30 mg if the Factor VIII level is above at least one reference value, wherein the reference value is a Factor VIII level of between 50% and 200%, 60% and 200%, 50% and 75%, 75% and 100%, 70% and 200%, 80% and 175%, 80% and 160%, or between 80% and 140%, or 150% and 200 or 250%, preferably between 100% and 200% of Factor VIII level in standard plasma as described herein.

Preferably the means involve an ELISA assay, one-stage clotting assay or chromogenic assay, preferably an ELISA assay.

The present disclosure is preferably not directed to use in a subject with inherited bleeding disorder, such as hemophilia A, hemophilia B or Von Willebrand disease.

Further disclosure

1. Method of detecting Factor VIII level in a sample obtained from a subject in need of treatment with at least one Factor Xa inhibitor, the method comprising:
   (a) selecting at least one subject in need of treatment with at least one Factor Xa inhibitor;
   (b) detecting Factor VIII level in a sample obtained from the at least one subject.

2. Method according to item 1, wherein step (b) is to determine an appropriate dosage of the at least one Factor Xa inhibitor, preferably wherein the dosage per day of the at least one Factor Xa inhibitor is
   between 1 mg and 10 mg if the Factor VIII level is below at least one reference value; or
   between 10 mg and 30 mg if the Factor VIII level is above at least one reference value.

3. Method according to item 2, wherein the reference value is a Factor VIII level of between 100% and 200% of Factor VIII level in standard plasma.

4. Method according to any one of the previous items, further comprising step (c) of administering at least one Factor Xa inhibitor to the subject, preferably once or twice daily.

5. Method according to any one of the previous items, wherein the at least one Factor Xa inhibitor is for the treatment of at least one condition chosen from the group consisting of: thrombosis, venous thrombosis, thromboembolic disease, thrombosis prophylaxis particularly after surgery, cardiovascular disease, atrium fibrillation, coronary artery disease, angina pectoris, angina infarction, myocardial infarction, stroke, ischemic stroke, cerebral infarction, transient ischemic attack, cancer-associated thrombosis, and pulmonary embolism.

6. Method according to any one of the previous items, wherein step (b) is performed before and/or during treatment of the at least one subject with the at least one Factor Xa inhibitor.

7. Method according to any one of the previous items, wherein the at least one Factor Xa inhibitor is chosen from the group consisting of apixaban, rivaroxaban, and edoxaban, wherein preferably the Factor Xa inhibitor is apixaban.

8. Method according to any one of the previous items, wherein the sample is a body fluid sample, wherein the body fluid sample preferably is chosen from the group consisting of blood sample and blood plasma sample.

9. Method according to any one of the previous items, wherein detecting Factor VIII is performed by an ELISA assay, one-stage clotting assay or chromogenic assay, preferably an ELISA assay.

10. Method according to any one of the previous items, wherein step (b) is repeated at least one, two, three, five or ten time(s) preferably with interval(s) of between 1-500, 5-250, or 10-100 days.

11. Method according to any one of the previous items, wherein the method is performed in vitro and/or ex vivo.

12. Use of a kit comprising means for detecting Factor VIII, for determining an appropriate dosage of at least one Factor Xa inhibitor for a subject in need of treatment with at least one Factor Xa inhibitor.

13. Use according to item 12, wherein the means involve an ELISA assay, one-stage clotting assay or chromogenic assay, preferably an ELISA assay.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

DETAILED DESCRIPTION

Figure 1:
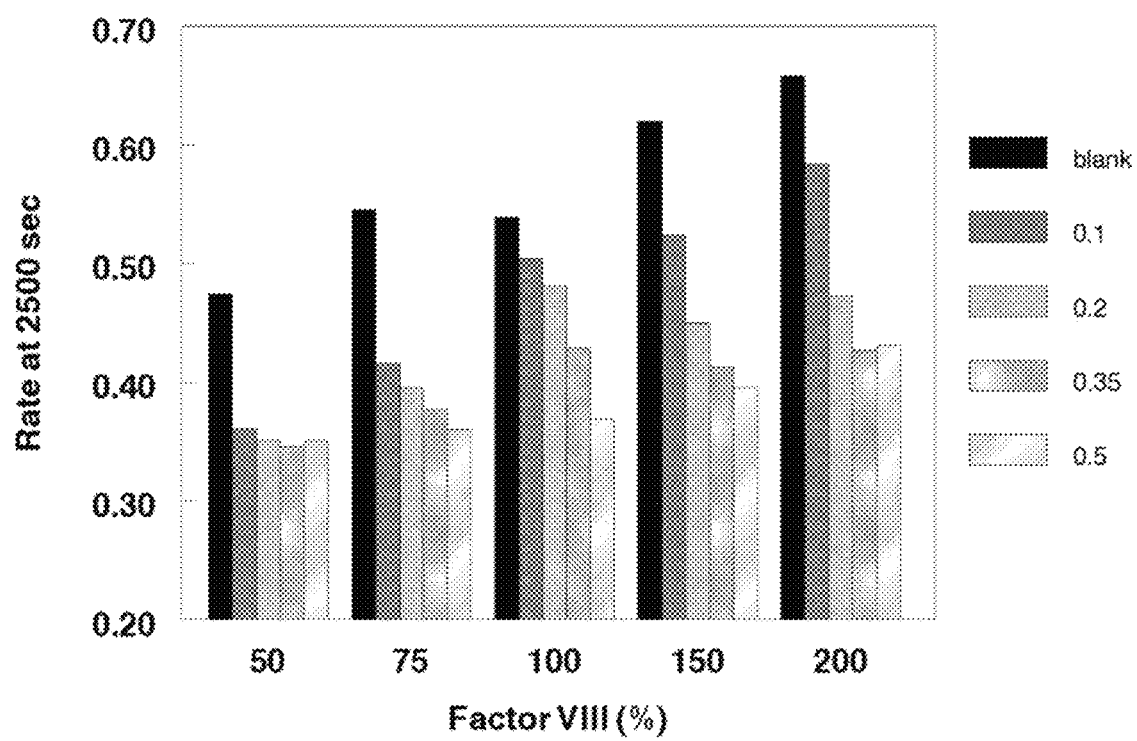
FIG. 1: For five different Factor VIII concentrations, i.e., 50%, 75%, 100%, 150% or 200%, five bars are shown representing subsamples to which apixaban was added to a different total concentration, i.e., 0 µM, 0.1 µM, 0.2 µM, 0.35 µM, or 0.5 µM, respectively.

It can be observed that for a Factor VIII level of below 100%, the lowest apixaban concentration already achieves close to maximal inhibition of clot growth rate. Here, treatment with a low apixaban concentration is indicated (in plasma: 0.1 µM) to not create a bleeding risk. For factor VIII levels above 100%, 0.1 µM apixaban will not be very effective and 0.35 µM in plasma is suggested for substantial inhibition. Here, the treatment is aiming at reducing thrombosis risk.

Experimental Section

Clot Growth Rate Assay

The clot growth rate assay monitors over time fibrin clot development in a nonstirred thin layer of platelet-free plasma activated by immobilized tissue factor. For this, the Thrombodynamics Basic Kit can be used as an in vitro diagnostic kit used to perform measurements of spatiotemporal dynamics of fibrin clot formation in blood plasma samples. The kit consists of measurement cuvettes, activating inserts and reagents for samples treatment. The kit is obtainable from HemaCore intended for professional use in the laboratory on the Thrombodynamics Analyzer T-2. See, for further details, Soshitova et al. (Blood Coagul. Fibrinolysis, 2012 September; 23(6):498-507).

Factor VIII Measurement Assays

Rapid ELISA Assay

The VisuLize™ FVIII Antigen Kit (Affinity Biologicals Inc.) can be used to quantitatively measure Factor VIII in human plasma. It has the following features:
   Rapid sandwich ELISA to measure FVIII (F8) antigen (FVIII:Ag)
   1 hour 55 minutes total incubation time
   FVIII:Ag reported as International Units/ml traceable to WHO standard for FVIII antigen
   Detection limit to 0.008 IU/ml FVIII:Ag (0.8%)
   Includes normal and low controls
   Shelf-life: 18 months
   Semin. Thromb. Hemost. 2002 June; 28(3):247-56.
   This rapid ELISA assay is described extensively by O'Donnell et al. (Thromb. Haemost. 1997; 77:825-828). Alternatively, the Human Factor VIII total antigen assay ELISA kit can be used (Molecular Innovations).

One-Stage Clotting Assay

The one-stage clotting assay is originally described in 1953 (Langdell et al., Translational Research, 1953, Vol. 41, Issue 4, pages 637-647) and later modified into the activated partial thromboplastin time (APTT). The principle is to measure by what extent a plasma sample corrects the prolonged coagulation time of FVIII-deficient plasma in an APTT-based assay.

In the one-stage assay, FVIII-deficient plasma is added to test plasma and the APTT reagent, mixed and incubated for 3-5 minutes. This is the contact activation phase during which factor XI (FXI) is activated, but little happens to FVIII. The mixture is then recalcified, and the coagulation time is recorded. This takes approximately 40-140 seconds depending on the APTT assay and the FVIII content. To determine the FVIII:C, the clotting time is compared to a standard curve, which is constructed by plotting the clotting times of serial dilutions of standard plasma (FVIII 0-200%) vs. factor VIII activity on logarithmic/linear scale graph paper. The World Federation of Haemophilia (WFH) recommends a parallel line analysis where identical dilutions of the test and standard plasma are compared (see S. Kitchen, A. McCraw, M. Echenagucia, on behalf of the WFH Laboratory Sciences Committee, Diagnosis of Hemophilia and Other Bleeding Disorders: A Laboratory Manual, 2nd edn. Montreal, Québec, Canada: World Federation of Hemophilia, 2010). The parallel line analysis decreases variability and increases precision. The one-stage clotting assay is extensively described in Laboratory Techniques in Thrombosis—a Manual (Jespersen, ed., Bertina, and Haverkate; Springer Science+Business Media Dordrecht 1999).

Chromogenic Assay

This assay involves a first incubation stage wherein FVIII activity is rate limiting to generate FXa and a second stage to determine the amount of FXa produced. A reagent containing purified coagulation factors (FIXa, FX and thrombin) in optimal concentrations is used in the first stage, which does not rely on the extrinsic or intrinsic initiation pathways as the thrombin activates FVIII. The amount of FXa generated in the first stage is measured by its action on a specific chromogenic substrate, which releases a chromophore upon cleavage that absorbs light of a certain wavelength. The color intensity produced is directly proportional to the amount of FXa, which, in turn, is directly proportional to the FVIII activity in the sample (see also S. Rosen, M. Chiarion Casoni, Chromogenic determination of factor VIII activity in plasma and factor VIII concentrates. Chromogenic Monograph Series). The chromogenic assay is extensively described in Laboratory Techniques in Thrombosis—a Manual (Jespersen, ed., Bertina, and Haverkate; Springer Science+Business Media Dordrecht 1999).

Plasma Level of Factor VIII Indicates the Appropriate Dose for any Factor Xa Inhibitor Five plasma samples were prepared containing 50%, 75%, 100%, 150%, or 200% Factor VIII, respectively. The samples were prepared using FVIII-deficient plasma, normal plasma from healthy subjects, and FVIII concentrate and Factor VIII levels were measured and confirmed by the one-stage clotting assay. Each of these five plasma samples was subdivided into five subsamples to which apixaban was added to a total concentration of 0 µM, 0.1 µM, 0.2 µM, 0.35 µM, or 0.5 µM in plasma, respectively. The 25 subsamples were subjected to a clot growth assay as described above, and the clot growth rate was measured at 2500 seconds after start of growth.

Results are shown in FIG. 1. For each different Factor VIII concentration (i.e., 50%, 75%, 100%, 150% or 200%), five bars are shown representing subsamples to which apixaban was added to a different total concentration, i.e., 0 µM, 0.1 µM, 0.2 µM, 0.35 µM, or 0.35 µM, respectively.

Figure 3:
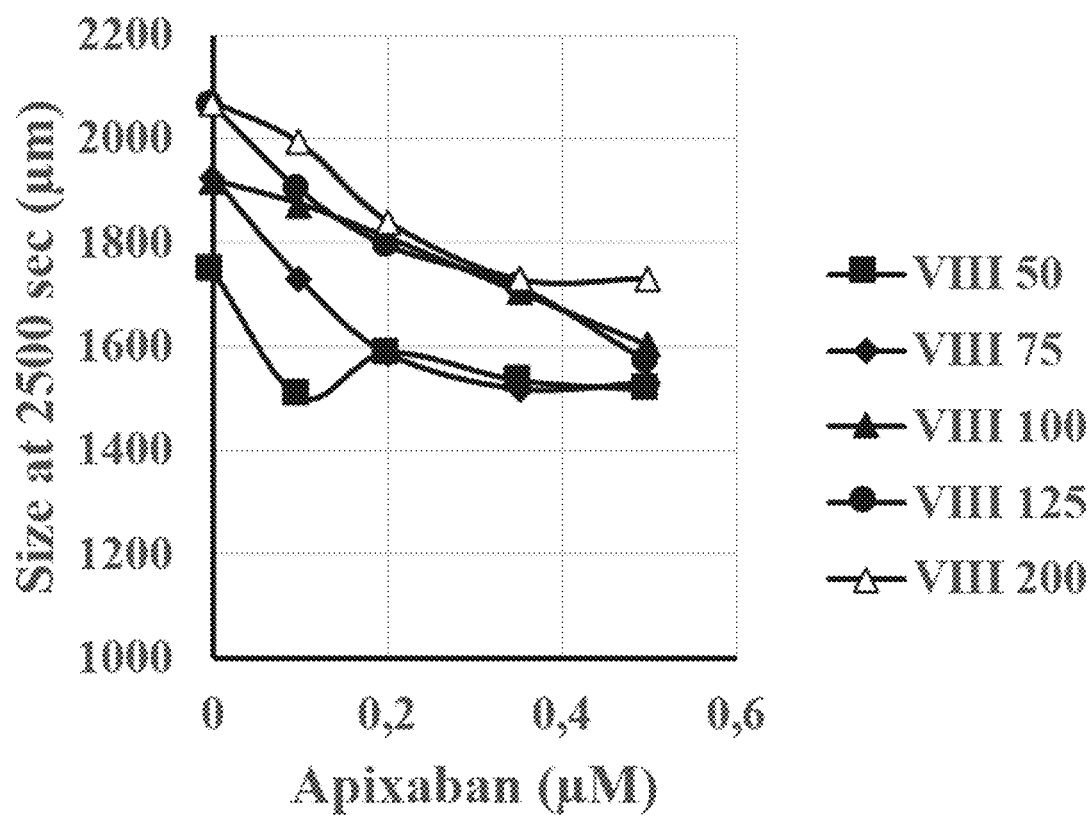
FIGS. 3 and 4: Clot size was measured for each different Factor VIII concentration (i.e., 50%, 75%, 100%, 150% or 200%) and apixaban concentration (0 µM, 0.1 µM, 0.2 µM, 0.35 µM, or 0.35 µM).
Figure 4:
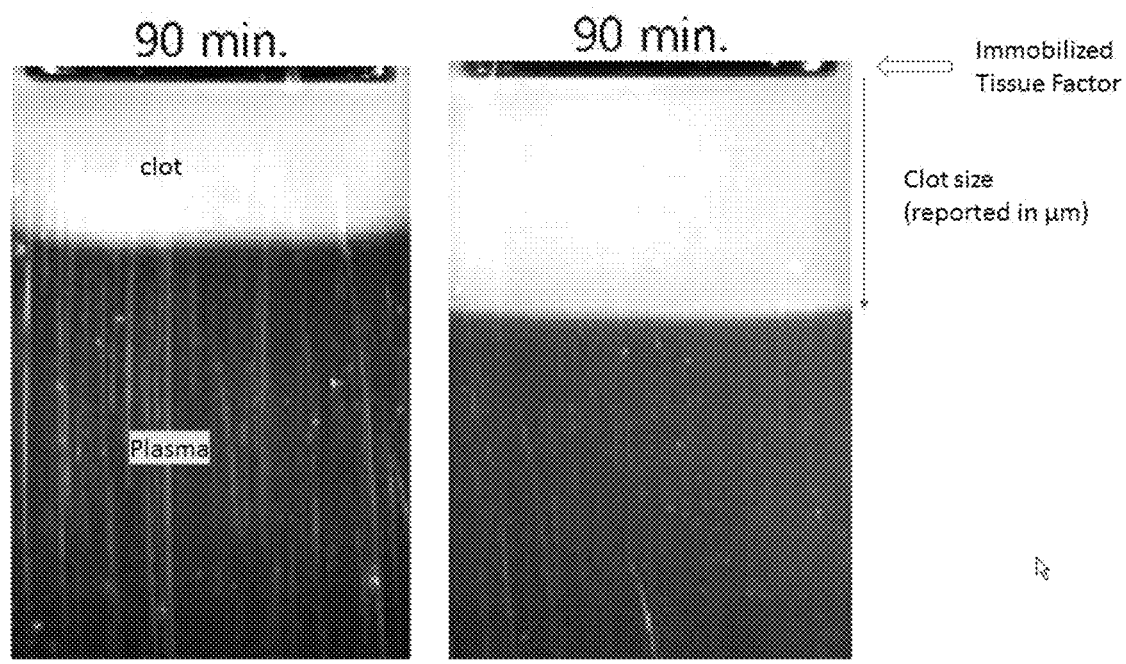

Similarly, for each different Factor VIII concentration (i.e., 50%, 75%, 100%, 150% or 200%) and apixaban concentration (0 µM, 0.1 µM, 0.2 µM, 0.35 µM, or 0.35 µM), clot size was measured (FIGS. 3 and 4).

It can be observed that for a Factor VIII level of below 100%, the lowest apixaban concentration already achieves close to maximal inhibition of clot rate. Here, treatment with a low apixaban concentration is indicated (in plasma: 0.1 µM) to not create a bleeding risk. For factor VIII levels above 100%, 0.1 µM apixaban will not be very effective and 0.35 µM is suggested for substantial inhibition. Here, the treatment is aiming at reducing thrombosis risk.

Figure 2:
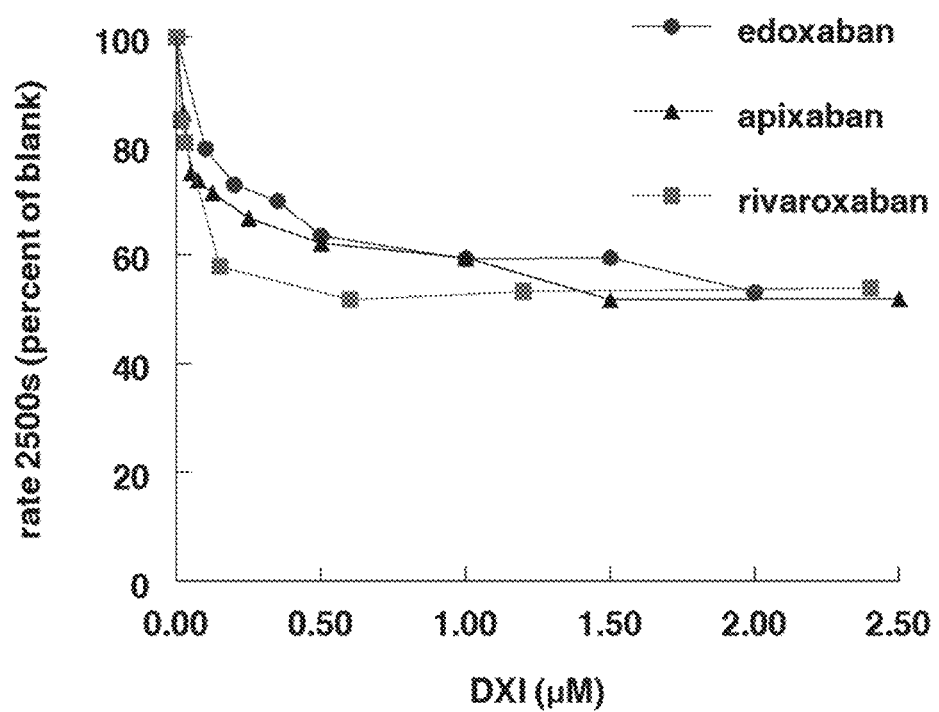
FIG. 2: Edoxaban and rivaroxaban both closely mimic the effects of apixaban in the clot growth rate assay.

The results will be the same in case of other Factor Xa inhibitors than apixaban. Apixaban and other Factor Xa inhibitors (such as edoxaban and rivaroxaban) share the same mechanism of action. As can be seen in FIG. 2, edoxaban and rivaroxaban both closely mimic the effects of apixaban in the clot growth rate assay.

Different Dosages of Factor Xa for Patients with Different Factor VIII Levels

Four subjects in need of Factor Xa treatment are selected, including three patients with thrombosis, and one patient with coronary artery disease. Measurement of Factor VIII (by the rapid ELISA assay as described herein) in the subjects reveals:

| Subject for Factor Xa treatment | Factor VIII level |
|---|---|
| Patient 1 (thrombosis) | 80% of Factor VIII level in standard plasma* |
| Patient 2 (thrombosis) | 95% of Factor VIII level in standard plasma* |
| Patient 3 (thrombosis) | 220% of Factor VIII level in standard plasma* |
| Patient 4 (coronary artery disease) | 240% of Factor VIII level in standard plasma* |

*WHO International Standard plasma (07/316)

To verify that plasma levels of Factor VIII indeed indicate the appropriate dose for any Factor Xa inhibitor as proposed herein (in this case by using a reference value of 150% of Factor VIII level in standard plasma), the following Factor Xa dosage is prescribed, either according to the disclosure or not according to the disclosure:

Dosage According to the Present Disclosure

| Subject for Factor Xa treatment | Factor Xa dosage per day |
|---|---|
| Patient 1 (thrombosis) | between 1-10 mg Apixaban (in this case 5 mg) |
| Patient 3 (thrombosis) | between 10 mg and 30 mg Edoxaban (in this case 20 mg) |

Dosage not According to the Present Disclosure

| Subject for Factor Xa treatment | Factor Xa dosage per day |
|---|---|
| Patient 2 (thrombosis) | between 10 mg and 30 mg Edoxaban (in this case 20 mg) |
| Patient 4 (coronary artery disease) | between 1 mg and 10 mg Apixaban (in this case 5 mg) |

Patients 1 and 3 thus receive a Factor Xa dosage in accordance with the present disclosure, while patients 2 and 4 do not. Coagulation status of patients 1-4 is determined by a routine coagulation test (activated partial thromboplastin time, APTT).

Coagulation status of patients 1 and 3 reveals no increased risk of blood clotting or bleeding events. However, coagulation status of Patient 2 reveals an increased risk of bleeding events and coagulation status of Patient 4 reveals an increased risk of blood clotting events.

It can be concluded that plasma levels of Factor VIII indeed indicate the appropriate dose for any Factor Xa inhibitor as proposed herein.

The invention claimed is:

1. A method of treating a subject having thrombosis or thrombosis risk in need of treatment with apixaban, the method comprising:
   detecting Factor VIII level in a sample obtained from the subject to determine an appropriate dosage of the apixaban, and
   administering to the subject:
      a dose of 5 mg of apixaban per day if the Factor VIII level detected in the sample is below at least one reference value; or
      a dose of 20 mg of apixaban per day if the Factor VIII level detected in the sample is above at least one reference value,
   wherein the reference value is a Factor VIII level of between 100% and 200% of Factor VIII level in standard plasma.

2. The method according to claim 1, wherein the apixaban is to be administered to the subject once or twice daily.

3. The method according to claim 1, wherein detecting the Factor VIII level is performed before and/or during treatment of the at least one subject with the apixaban.

4. The method according to claim 1, wherein the sample is a body fluid sample selected from the group consisting of a blood sample and a blood plasma sample.

5. The method according to claim 1, wherein detecting the Factor VIII level is repeated at least once.

6. A method of treating a subject having thrombosis or thrombosis risk with apixaban, the method comprising:
   administering to the subject:
      a dose of 5 mg of apixaban per day when a Factor VIII level detected in a blood sample and/or a blood plasma sample taken from the subject is less than a Factor VIII level of between 100% and 200% of Factor VIII level in standard plasma; or
      a dose of 20 mg of apixaban per day when a Factor VIII level detected in a blood sample and/or a blood plasma sample taken from the subject is greater than a Factor VIII level of between 100% and 200% of Factor VIII level in standard plasma.

* * * * *